United States Patent
Mower

(10) Patent No.: US 6,178,351 B1
(45) Date of Patent: Jan. 23, 2001

(54) ATRIAL SENSING AND MULTIPLE SITE STIMULATION AS INTERVENTION MEANS FOR ATRIAL FIBRILLATION

(75) Inventor: Morton M. Mower, Baltimore, MD (US)

(73) Assignee: The Mower Family CHF Treatment Irrevocable Trust, Baltimore, MD (US)

( * ) Notice: Under 35 U.S.C. 154(b), the term of this patent shall be extended for 0 days.

(21) Appl. No.: 09/228,262

(22) Filed: Jan. 11, 1999

Related U.S. Application Data

(63) Continuation-in-part of application No. 08/699,552, filed on Aug. 19, 1996, now Pat. No. 5,871,506.

(51) Int. Cl.$^7$ ............................................. A61N 1/39
(52) U.S. Cl. ........................................................... 607/5
(58) Field of Search .................... 607/4, 5, 7, 28; 128/898

(56) References Cited

U.S. PATENT DOCUMENTS

| | | | |
|---|---|---|---|
| 3,924,641 | 12/1975 | Weiss | 128/419 |
| 3,946,745 | 3/1976 | Hsiang-Lai et al. | 128/421 |
| 4,343,312 | 8/1982 | Cals et al. | 128/419 |
| 4,402,322 | 9/1983 | Duggan | 128/419 |

(List continued on next page.)

FOREIGN PATENT DOCUMENTS

| | | | |
|---|---|---|---|
| 491649 A2 | 6/1992 | (EP) | A61N/1/39 |
| 0600631 A2 | 11/1993 | (EP) | A61N/1/368 |
| 813889 A2 | 12/1997 | (EP) | A61N/1/368 |
| 2763247 A1 | 5/1997 | (FR) | A61N/1/365 |
| 93/01861 | 2/1993 | (WO) | A61N/1/36 |
| 97/25098 | 7/1997 | (WO) | A61N/1/00 |

OTHER PUBLICATIONS

Estes et al. Implantable Cardioverter–Defibrillatrs 1994 p. 181.

Ravazzi et al. Changes Induced in Ventricular Activator Using Non–Standard Pacing Pulse Morphologies at Different Right Septal Sites. 1998.

Ravazzi, et al. Ventricular Pacing Threshold Improvement Using Non–Standard Pacing Pulse Morphologies at Different Right Septal Sites. 1998.

Prochaczek et al. Transcutaneous Ventricular Pacing of the Human Heart with Increased Overthreshold Energy; Hemodynamic Effects 1998.

Kutarski et al. Cathode or Anode in Coronary Sinus (CS) in Pts With Daubert's BiA Pacing System? 1998.

Primary Examiner—Jeffrey R. Jastrzab
(74) Attorney, Agent, or Firm—Roberts Abokhair & Mardula LLC

(57) ABSTRACT

Atrial sensing and stimulation as intervention for atrial fibrillation. The present invention relates to a method of atrial defibrillation. In a variety of protocols varying combinations of conventional and biphasic stimulation are applied at threshold and sub-threshold levels. In a preferred embodiment, the implantable electronic stimulation device of the present invention includes multiple electrodes having stimulating and sensing capabilities. The small size of these electrodes allows for intravenous insertion into the patient.

37 Claims, 6 Drawing Sheets

U.S. PATENT DOCUMENTS

| | | | |
|---|---|---|---|
| 4,498,478 | 2/1985 | Bourgeois | 128/419 |
| 4,539,991 | 9/1985 | Boute et al. | 128/419 PG |
| 4,545,956 | 10/1985 | Herscovoci | 128/419 |
| 4,569,350 | 2/1986 | Mumford et al. | 128/697 |
| 4,781,194 | 11/1988 | Elmqvist | 128/419 PG |
| 4,903,700 | 2/1990 | Whigham et al. | 128/419 |
| 4,940,054 | 7/1990 | Grevis et al. | 128/419 PG |
| 4,944,298 | 7/1990 | Sholder | 128/419 PG |
| 5,027,815 | 7/1991 | Funke et al. | 128/419 PG |
| 5,111,811 | 5/1992 | Smits | 128/419 D |
| 5,163,429 | 11/1992 | Cohen | 128/419 PG |
| 5,181,511 | 1/1993 | Nickolls et al. | 128/419 PG |
| 5,193,535 | 3/1993 | Bardy et al. | 128/419 D |
| 5,213,098 | 5/1993 | Bennett et al. | 128/419 PG |
| 5,215,083 | 6/1993 | Drane et al. | 128/419 D |
| 5,224,475 | 7/1993 | Berg et al. | 128/419 D |
| 5,391,185 | 2/1995 | Kroll | 607/4 |
| 5,411,547 | 5/1995 | Causey, III | 607/129 |
| 5,421,830 | 6/1995 | Epstein et al. | 607/30 |
| 5,480,413 | 1/1996 | Greenhut et al. | 607/14 |
| 5,514,161 | 5/1996 | Limousin | 607/9 |
| 5,522,858 | 6/1996 | van der Veen | 607/14 |
| 5,534,015 | 7/1996 | Kroll et al. | 607/7 |
| 5,562,708 | 10/1996 | Combs et al. | 607/4 |
| 5,601,608 | 2/1997 | Mouchawar | 607/5 |
| 5,620,471 | 4/1997 | Duncan | 607/14 |
| 5,649,966 | 7/1997 | Noren et al. | 607/14 |
| 5,713,929 | 2/1998 | Hess et al. | 607/14 |
| 5,814,079 | 9/1998 | Kieval | 607/4 |
| 5,871,506 | 2/1999 | Mower | 607/9 |

ATRIAL SENSING AND MULTIPLE SITE STIMULATION AS INTERVENTION MEANS FOR ATRIAL FIBRILLATION

RELATED APPLICATION DATA

The present disclosure is a continuation-in-part application related to the U.S. Patent Application entitled "Augmentation of Electrical Conduction and Contractility by Biphasic Cardiac Pacing", Ser. No. 08/699,552, filed Aug. 19, 1996 now U.S. Pat. No. 5,871,506.

FIELD OF THE INVENTION

The present invention relates generally to electronic stimulation devices to control the beating of hearts, especially hearts with pathologies that interfere with normal rhythmicity, electrical conduction, and/or contractility. In particular, the present invention relates to pacemakers used to overcome atrial fibrillation by use of 1) atrial sensing; 2) electrical test stimulation of the atria; and 3) multiple site stimulation in which the various atrial areas are slowly entrained to a common beating rate to produce electrical/functional conformity, i.e., cardioversion, with each case either eventuating in spontaneous reversion to a normal atrial rhythm, or reduced energy requirement for reversion by electrical countershock.

BACKGROUND OF THE INVENTION

Morbidity associated with malfunctions of the atria, while not immediate, is high. Atrial malfunctions of rhythmicity (e.g., atrial fibrillation, various atrial arrhythmias, A-V block and other conduction abnormalities, etc.) can contribute to thrombosis, emboli, stroke and/or heart failure, each of which can place a patient in significant peril.

Atrial Sensing. A variety of approaches have been developed which use pacemakers to counter atrial malfunctions of rhythmicity, as well as attendant effects on ventricular function. In addition, sophisticated approaches have been developed for pacemaker systems to determine the nature of any particular ventricular malfunction, and whether a malfunction originates in the atria or in the ventricles. One such approach uses ventricular sensing to measure/determine the probability density function (pdf) on a moment-to-moment basis. For example, U.S. Pat. No. 5,163,429 to Cohen discloses the use of narrow window pdf data as but one criterion among several for assessing ventricular cardiac function. The use of pdf data to determine ventricular fibrillation also is disclosed in *Implantable Cardioverter-Defibrillators* (N. A. Estes III, A. Manolis & P. Wang, ed.). U.S. Pat. No. 5,421,830 to Epstein, et al. (discussed further below) also discloses the use of pdf data as one set among a variety of data types that collectively are also used to assess cardiac function. The use of probability density function data for assessing atrial cardiac function has not been disclosed and presents its own unique difficulties as will be further discussed.

Electrical Test Stimulation of Atria. In a few limited cases, pacemaker protocols have been employed in which electrical test stimuli are applied to the atria, and the physiological responses thereto are monitored to aid in the determination of the best or most appropriate protocol to initiate, cure, or ameliorate the existing cardiac malfunction. For example, U.S. Pat. No. 5,620,471 to Duncan discloses three basic protocols for determining whether observed ventricular irregularities are actually caused by atrial arrhythmias. One protocol includes atrial electrical test stimulation, and all three protocols monitor both atrial and ventricular rhythms for three parameters: rates of atrial and ventricular firing, stability of firing/beating in atria and ventricles, and whether or not ventricular firing tracks atrial firing. In the first protocol, when the ventricular firing rate is less than the atrial firing rate (indicating no ventricular tracking of atrial beats), and firing rates are stable, then ventricular tachycardia is presumed, and ventricular stimulation is applied. On the other hand (second protocol), if the ventricular firing rate is not stable, then atrial arrhythmia is presumed, and atrial stimulation is applied. The third protocol is based on the fact that, when the ventricular firing rate equals the atrial firing rate, there may or may not be ventricular tracking of atrial firing. Whether or not there is ventricular tracking is determined by the presence or not of ventricular tracking following premature atrial stimulation by the pacemaker. If there is ventricular tracking of atrial firing, the arrhythmic mechanism is presumed to be atrial tachycardia. However, if there is no ventricular tracking of atrial firing, then ventricular tachycardia is presumed, and ventricular stimulation is performed.

U.S. Pat. No. 5,421,830 to Epstein, et al. discloses a general means for recording, testing, and analyzing cardiac function based on data from—and electrical test stimulation via—a patient's pacemaker, as well as data from additional sensors detecting hemodynamic or other body functions. Total intracardiac electrograms (reflecting both atrial and ventricular functional status) or just selected data (e.g., P-P or R-R intervals, heart rate, arrhythmia duration, slew rate, probability density function, etc.) may be recorded and analyzed. The patient's atrial and ventricular responses to electrical test pulses may also be recorded. In sum, this system provides a means to more easily tailor settings for pacemakers to achieve optimal settings for the specific patient or for the specific situation (e.g., during exercise or exertion) of a given patient.

U.S. Pat. No. 5,215,083 to Drane, et al. also discloses the use of electrical test stimulation to aid in the fine tuning and evaluation of different possible stimulation protocols for a patient's heart. In particular, electrical test pulses are employed to induce ventricular fibrillation or tachycardia for use in evaluating the effectiveness of alternative programmed therapies.

Multiple Site Atrial Stimulation. The use of multiple site atrial stimulation has been disclosed for various purposes, such as defibrillation, cardioversion, pacing, and dc field production. One example is provided by U.S. Pat. No. 5,562,708 to Combs, et al., which discloses the employment of large surface electrodes (each effectively comprising multiple electrodes) that are implanted to one or both atria for providing extended, low energy electrical impulses. The electrical impulses are applied simultaneously at multiple sites over atrial surfaces, and atrial fibrillation is interrupted by gradually entraining greater portions of atrial tissue. These pacemaker electrodes may be used for various purposes in addition to pacing, such as conventional defibrillation and cardioversion.

U.S. Pat. No. 5,649,966 to Noren, et al. discloses the use of multiple electrodes for the purpose of applying a sub-threshold dc field to overcome fibrillation. The rate of application of the dc field is sufficiently low so that no action potential is triggered. Polarity may also be changed periodically. In one embodiment, four electrodes are positioned within a single plane in the heart, which permits a dipole field in virtually any direction within that plane.

U.S. Pat. No. 5,411,547 to Causey, III discloses the use of sets of complex mesh patch electrodes, in which each electrode comprises an anode patch and a cathode patch, for purposes of cardioversion-defibrillation. Bidirectional cardiac shocking is permitted by these electrodes.

U.S. Pat. No. 5,391,185 to Kroll discloses the use of multiple electrodes to effect atrial defibrillation. The possibility of inducing ventricular fibrillation during the course of atrial defibrillation is greatly reduced by synchronizing the atrial stimulation to fall within the QRS phase of the ventricular cycle.

U.S. Pat. No. 5,181,511 to Nickolls, et al. discloses the use of multiple electrodes in antitachycardia pacing therapy. The electrodes not only each serve an electrical sensing role (to locate the site of an ectopic focus), but also function in concert to create a virtual electrode for stimulating at the site of an ectopic focus.

Existing Needs. In the area of atrial malfunctions of rhythmicity what is needed is a means to entrain multiple atrial sites, but also in combination with an atrial sensing/measurement capability that is coupled with atrial test stimulation and analysis capability. Atrial test stimulation and analysis capability is needed to provide better determination of the nature of the malfunction and the most probable or efficacious corrective therapy to undertake. Furthermore, the use of atrial test stimulation is critically needed for the fundamental reason that the physician cannot know a priori how a given heart (or a given heart under a particular medical or pathological condition) will respond to a selected stimulation regime, even if that selected stimulation regime would work generally for other cardiac patients. Thus, a trial-and-error testing capability needs to be available for pacemakers whose traditional stimulation regimes do not work for the occasional refractory patient. The multiple site stimulation capability is needed in order to more quickly and efficiently cardioconvert the atria in the face of arrhythmia, fibrillation, etc. Atrial sensing and use of measurement data are needed to better provide the physician and/or the circuit logic of the pacemaker with information as to the physiological state of the heart; i.e., whether there is atrial arrhythmia or fibrillation, where an ectopic focus is located, etc. Thus, what is needed is a pacemaker that combines all three of these elements: atrial sensing and measurement capability, atrial electrical test stimulation and analysis capability, and multiple site stimulation capability.

Lastly, a need also exists for a stimulation protocol which can travel more quickly across the myocardium and which provides improved cardiac entrainment along with the ability to entrain portions of the heart from a greater distance.

SUMMARY OF THE INVENTION

It therefore is an object of the present invention to provide a pacemaker that is capable of pacing atria from multiple sites.

It is another object of the present invention to provide a pacemaker that is capable of slowly entraining atria by stimulating the atria at multiple sites to produce electrical and functional conformity of the atria, with resulting increased pumping efficiency of the heart.

It is yet another object of the present invention to provide a pacemaker that is capable of detecting the presence of atrial fibrillation and atrial arrhythmias by stimulating the atria and observing and measuring the consequent effects on atrial and ventricular function.

It is a further object of the present invention to provide a pacemaker that is capable of obtaining and analyzing probability density function data from atria in order to determine atrial rates of beating and to assess atrial physiological function.

It is a further object of the present invention to provide an electronic stimulation device, for stimulating the atria from multiple sites, where the electrodes of the electronic stimulation device can be inserted intravenously.

It is a further object of the present invention to provide an electronic stimulation device, for stimulating the atria from multiple sites, where each electrode of the device has an independent generator.

It is a further object of the present invention to provide an electronic stimulation device for stimulating the atria from multiple sites, where each site is entrained separately and quickly brought to the same phase.

It is a further object of the present invention to provide an electronic stimulation device for stimulating the atria from multiple sites, to sequence the sites to mimic a normal heart beat.

It is a further object of the present invention to determine cardiac capture by monitoring cardiac activity and noting when the baseline of such activity is off zero.

It is a further object of the present invention to decrease threshold rises due to a build up of fibrous tissue.

The present invention accomplishes the above objectives by providing a cardiac pacemaker with a unique constellation of features and capabilities. In particular, a means for entraining multiple atrial sites is provided by the use of multiple electrodes. The multiple electrodes not only permit multi-site stimulation capability, but also multi-site sensing (including pdf measurement) capability, which, by triangulation, essentially provides the ability to determine the site(s) of any atrial ectopic focus. The multi-site stimulation capability inherently provides a system poised for more efficient entrainment and/or cardioconversion of the atria in the face of arrhythmia, fibrillation, etc. Combined with this multi-site stimulation/sensing capability is the means to execute trial-and-error testing and analysis to determine the best general stimulation protocol, to fine tune a given protocol, or to adjust a protocol in response to changes in the physiological/pathological status of the patient in general and/or the patient's heart in particular.

Incorporating the use of biphasic stimulation with the present invention provides the additional benefits of reducing cardiac inflammation damage, reducing or eliminating threshold rises due to the buildup of fibrous tissue and extending battery life of the electrodes.

In addition, the ability to conduct trial-and-error testing, including the analysis of the data derived therefrom, permits more thorough and more definitive determination of the physiological status of the heart; this determination can practically approach a moment-to-moment basis when analysis is automated by appropriate software for the purpose.

In sum, the present invention provides a cardiac pacemaker that has greater functional capabilities for the patient's atria than current technologies allow. The greater atrial "coverage" from the strategic placement of multiple electrodes permits faster correction of atrial arrhythmia, fibrillation, etc. Similarly, the use of multi-site electrodes permits more accurate sensing, including the capability of locating the site(s) of any atrial ectopic focus so as to better apply corrective stimulation procedures. In addition, the ability to apply trial-and-error testing/analytical procedures permits quicker analysis and correction of malfunctions of electrical conduction, cardiac contractility, rhythmicity, etc. Thus, the present invention constitutes an advance in cardiac care procedures as they relate to atrial pacemakers. The end result for the patient is better treatment, and, hence, a better prognosis from the better and faster treatment.

The method and apparatus relating to biphasic pacing comprises a first and second stimulation phase, with each stimulation phase having a polarity, amplitude, shape, and duration. In a preferred embodiment, the first and second phases have differing polarities. In one alternative embodiment, the two phases are of differing amplitude. In a second alternative embodiment, the two phases are of differing duration. In a third alternative embodiment, the first phase is in a chopped wave form. In a fourth alternative embodiment, the amplitude of the first phase is ramped. In a fifth alternative embodiment the first phase is administered over 200 milliseconds after completion of a cardiac beating/pumping cycle. In a preferred alternative embodiment, the first phase of stimulation is an anodal pulse at maximum subthreshold amplitude for a long duration, and the second phase of stimulation is a cathodal pulse of short duration and high amplitude. It is noted that the aforementioned alternative embodiments can be combined in differing fashions. It is also noted that these alternative embodiments are intended to be presented by way of example only, and are not limiting.

Enhanced myocardial function is obtained through the biphasic stimulation of the present invention. The combination of cathodal with anodal pulses of either a stimulating or conditioning nature, preserves the improved conduction and contractility of anodal stimulation while eliminating the drawback of increased stimulation threshold. The result is a depolarization wave of increased propagation speed. This increased propagation speed results in increased synchronization and reduced heterogenicity of myocardial depolarization resulting in superior blood flow and contraction. Improved stimulation at a lower voltage level also results in: 1/ reduction in scar tissue buildup thereby reducing the tendency of the capture threshold to rise; 2/ reduction in power consumption leading to increased life for pacemaker batteries; and 3/ decreased potential for patient discomfort due to stimulation of the phrenic or diaphragmatic plexus or due to intercostal muscle pacing.

DESCRIPTION OF THE PREFERRED EMBODIMENTS

Electrical stimulation is delivered via lead(s) or electrode(s). These leads can be epicardial (external surface of the heart) or endocardial (internal surface of the heart) or any combination of epicardial and endocardial. Leads are well known to those skilled in the art. Lead systems can be unipolar or bipolar. A unipolar lead has one electrode on the lead itself, the cathode. Current flows from the cathode, stimulates the heart, and returns to the anode on the casing of the pulse generator to complete the circuit. A bipolar lead has two poles on the lead a short distance from each other at the distal end, and both electrodes lie within the heart.

Figure 1:
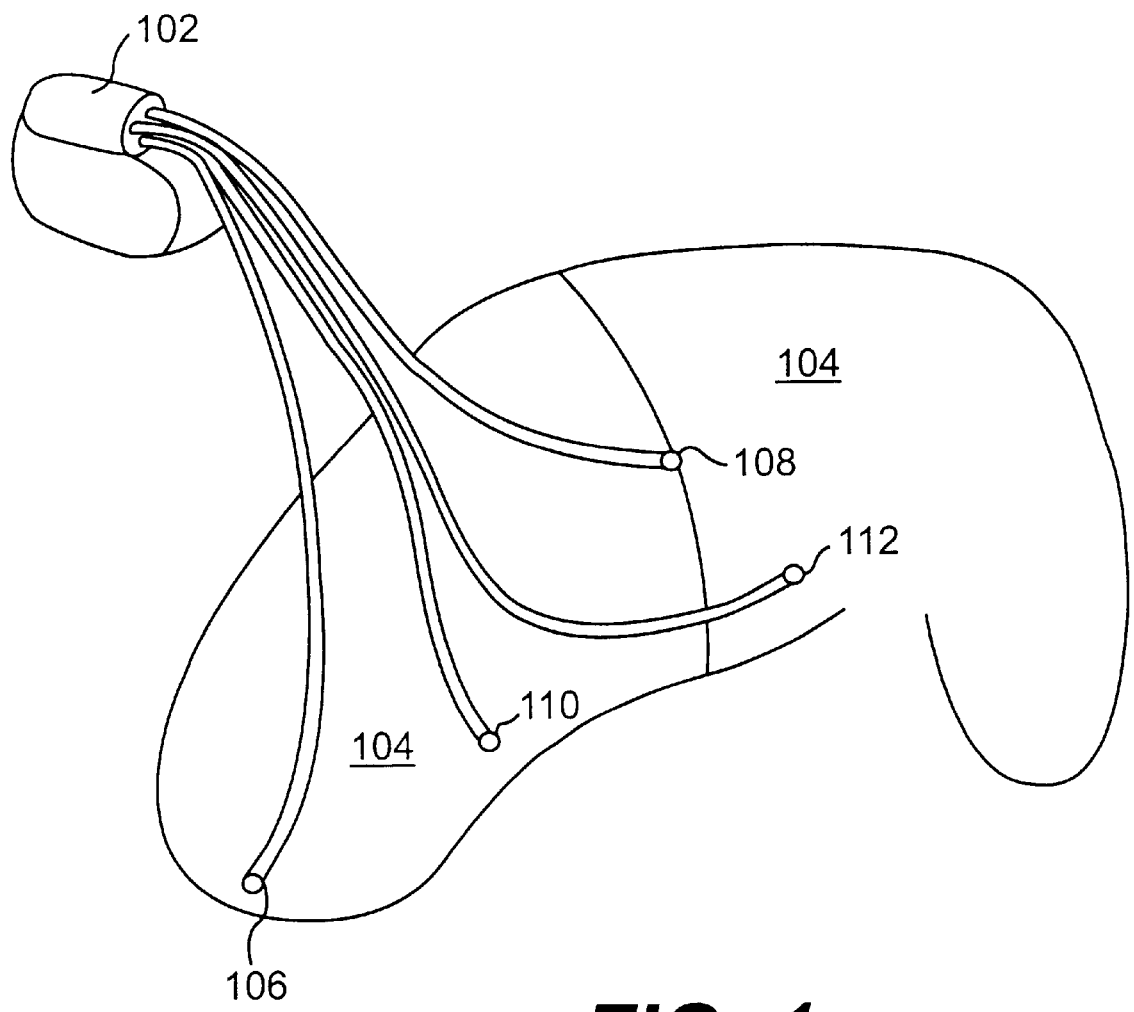
FIG. 1 illustrates the location of leads and electrodes in relation to a human heart.

FIG. 1 illustrates a plan view of implantable electronic stimulation device 102 and its associated lead and electrode system, in conjunction with human heart 104. As illustrated, the device includes right atrial appendage lead 106, right atrial septal lead 108, first coronary sinus lead 110 and second coronary sinus lead 112. Each of these multiple small electrodes can be inserted intravenously and includes an independent generator.

Figure 2:
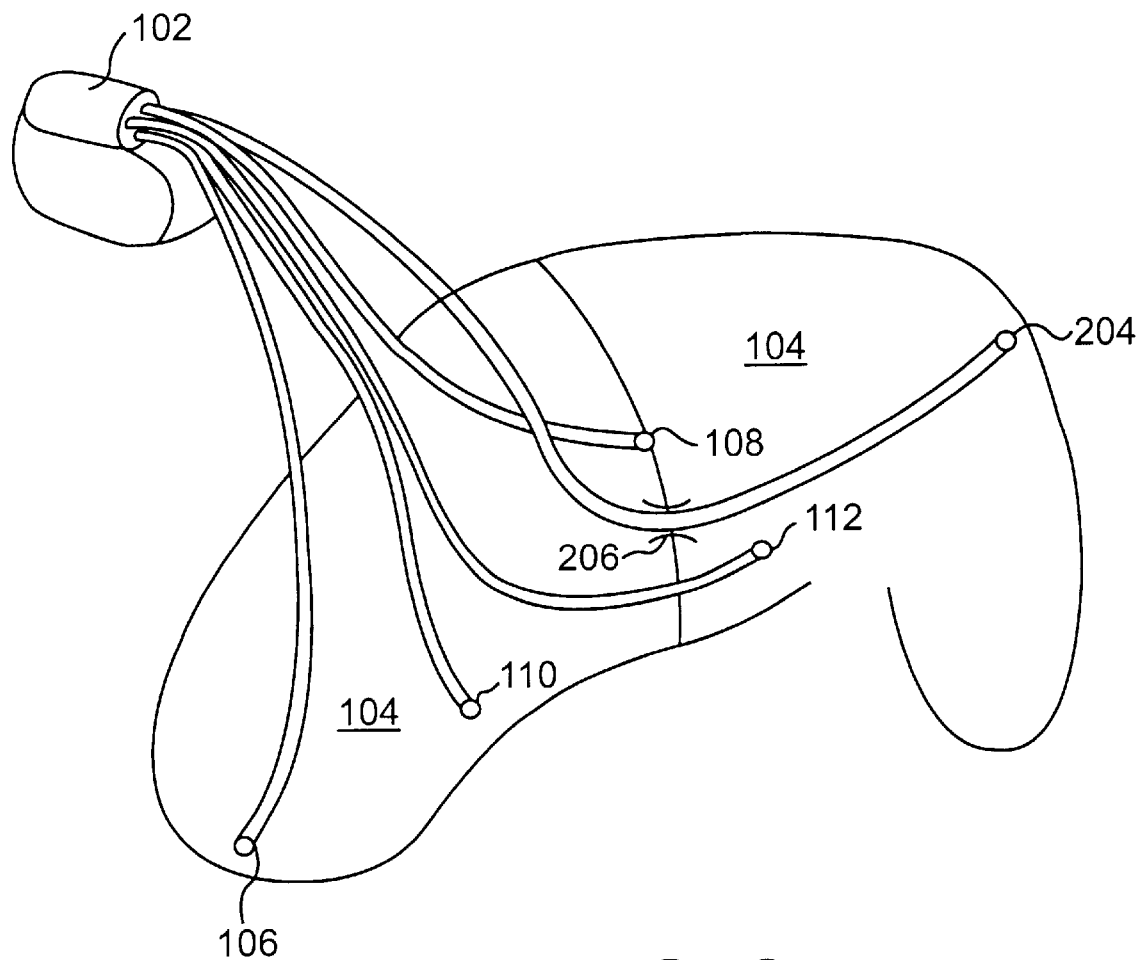
FIG. 2 illustrates an alternative location of leads and electrodes in relation to a human heart.

FIG. 2 illustrates a plan view of implantable electronic stimulation device 102 illustrating an alternative location of leads and electrodes in relation to human heart 104. As illustrated, the device includes right atrial appendage lead 106, right atrial septal lead 108, first coronary sinus lead 110, second coronary sinus lead 112 and left free wall lead 204. Each of these multiple small electrodes can be inserted intravenously and includes an independent generator. Because of the use of independent generators, each electrode can be timed differently. In a preferred embodiment, left free wall lead 204 is placed by piercing septum 206 and passing left free wall lead 204 through the septum to the left side of the heart. The aforementioned placement of leads is for illustration purposes only, and is not intended as a limitation. It is contemplated that multiple leads placed in a variety of locations could be used.

Each site (area of lead placement) can be entrained separately, and then brought to the same phase. In a preferred embodiment each site is gradually brought to the same phase; however, certain situations could require that each site is quickly brought to the same phase. In an alternative embodiment, the sites can be sequenced to mimic a normal heart beat. In addition to allowing multi-site stimulation capability, the sensing circuits of each electrode also allow for multi-site sensing. Through triangulation the multi-site sensing provides a means for determining the site(s) of any atrial ectopic focus.

In a preferred embodiment, stimulation is administered at threshold until capture has occurred, at which time stimulation is administered at a subthreshold level. In alternative embodiments, stimulation is: (1) initiated at threshold and remains at threshold; (2) initiated subthreshold and remains subthreshold; (3) conventional prior to capture and then biphasic; (4) biphasic prior to capture and then conventional or (5) biphasic throughout.

Threshold refers to the minimum voltage level (or pulse width using a fixed voltage) which succeeds in stimulating (capturing) the myocardium. To capture is to produce a driven beat because of the stimulus given. Thus, in the absence of the pulse, the beat would not have been produced. Pulses which do not capture are subthreshold, (even though they may be shown to perturb the membrane potential somewhat, and transiently). Subthreshold pulses thus may affect subsequent conduction, but not by the mechanism of initiating a driven beat. Generally, to determine threshold, voltage (or pulse width) is varied (upward or downward) until capture is gained or lost.

Conventional stimulation is well known to those skilled in the art and comprises monophasic waveforms (cathodal or anodal) as well as multiphasic waveforms wherein the nonstimulating pulses are of a minimal magnitude and are used, for example, to dissipate a residual charge on an electrode.

FIGS. 3 through 7 depict a range of biphasic stimulation protocols. These protocols have been disclosed in U.S. patent application Ser. No. 08/699,552 to Mower, which is herein incorporated by reference in its entirety.

Figure 3:
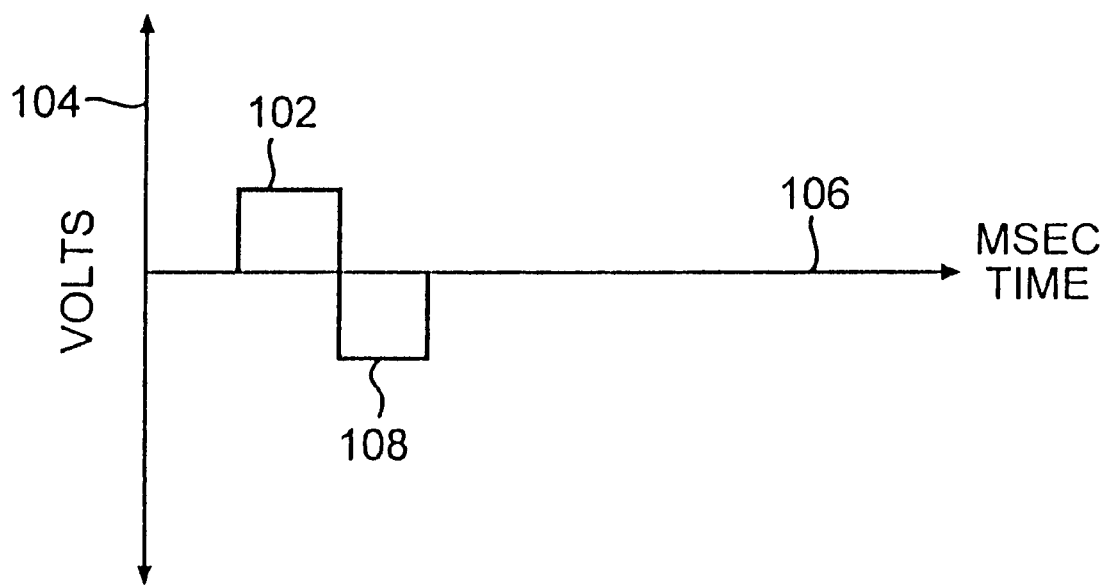
FIG. 3 is a schematic representation of leading anodal biphasic stimulation.

FIG. 3 depicts biphasic electrical stimulation wherein a first stimulation phase comprising anodal stimulus 302 is administered having amplitude 304 and duration 306. This first stimulation phase is immediately followed by a second stimulation phase comprising cathodal stimulation 308 of equal intensity and duration.

Figure 4:
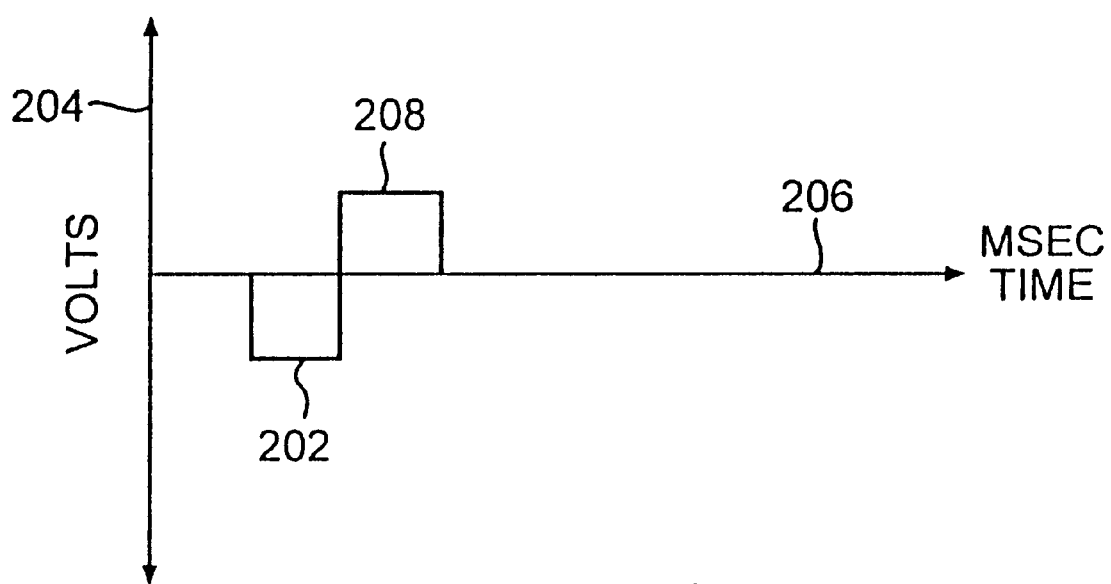
FIG. 4 is a schematic representation of leading cathodal biphasic stimulation.

FIG. 4 depicts biphasic electrical stimulation wherein a first stimulation phase comprising cathodal stimulation 402 having amplitude 404 and duration 406 is administered. This first stimulation phase is immediately followed by a second stimulation phase comprising anodal stimulation 408 of equal intensity and duration.

Figure 5:
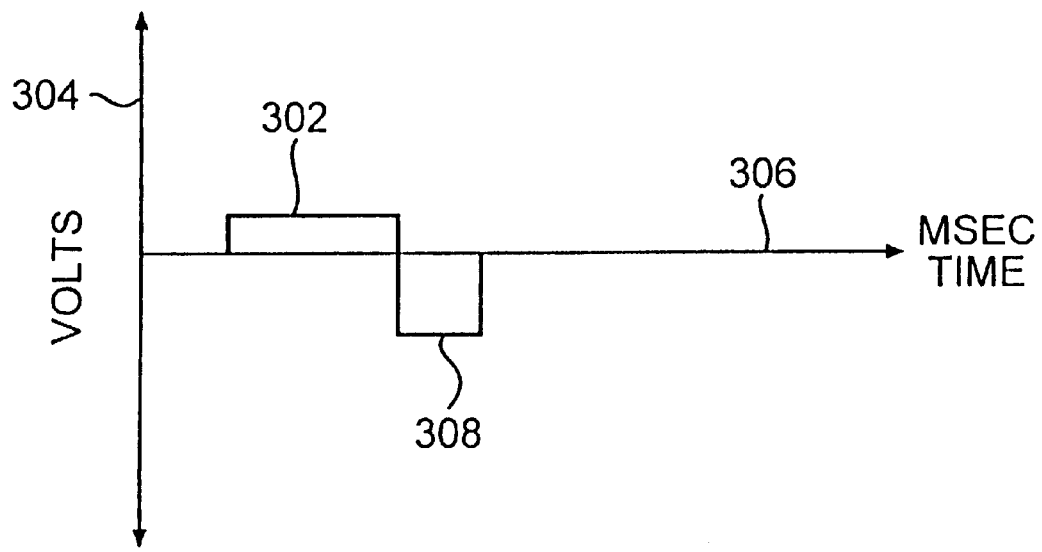
FIG. 5 is a schematic representation of leading anodal stimulation of low level and long duration, followed by conventional cathodal stimulation.

FIG. 5 depicts a preferred embodiment of biphasic stimulation wherein a first stimulation phase, comprising low level, long duration anodal stimulation 502 having amplitude 504 and duration 506, is administered. This first stimulation phase is immediately followed by a second stimulation phase comprising cathodal stimulation 508 of conventional intensity and duration. In differing alternative embodiments, anodal stimulation 502 is: 1) at maximum subthreshold amplitude; 2) less than three volts; 3) of a duration of approximately two to eight milliseconds; and/or 4) administered over 200 milliseconds post heart beat. Maximum subthreshold amplitude is defined for purposes of this application as the maximum stimulation amplitude that can be administered without eliciting a contraction. In a preferred embodiment, anodal stimulation is approximately two volts for approximately three milliseconds duration. In differing alternative embodiments, cathodal stimulation 508 is: 1) of a short duration; 2) approximately 0.3 to 1.5 milliseconds; 3) of a high amplitude; 4) in the approximate range of three to twenty volts; and/or 5) of a duration less than 0.3 millisecond and at a voltage greater than twenty volts. In a preferred embodiment, cathodal stimulation is approximately six volts administered for approximately 0.4 millisecond. In the manner disclosed by these embodiments, as well as those alterations and modifications which can become obvious upon the reading of this specification, a maximum membrane potential without activation is achieved in the first phase of stimulation.

Figure 6:
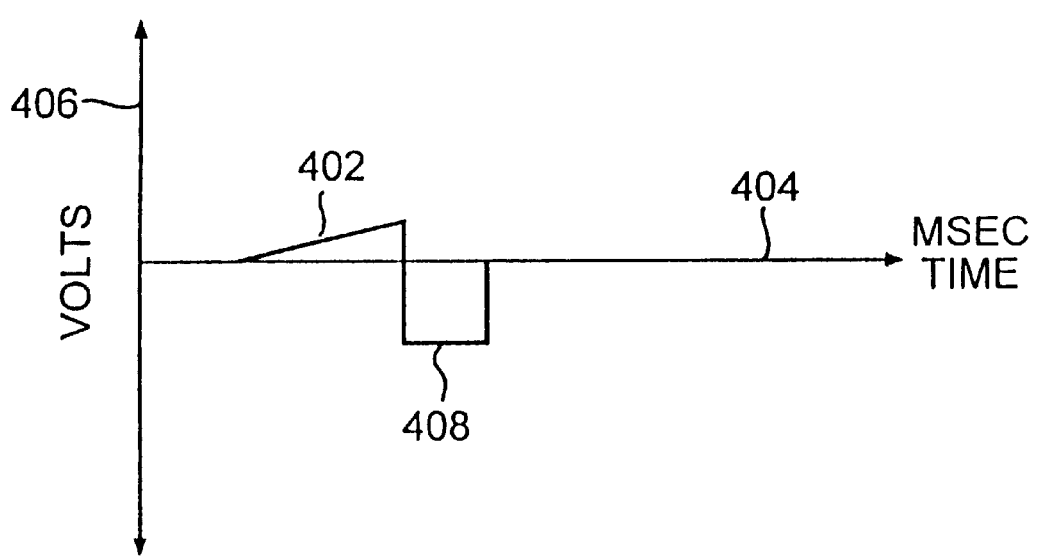
FIG. 6 is a schematic representation of leading anodal stimulation of ramped low level and long duration, followed by conventional cathodal stimulation.

FIG. 6 depicts an alternative preferred embodiment of biphasic stimulation wherein a first stimulation phase, comprising anodal stimulation 602, is administered over period 604 with rising intensity level 606. The ramp of rising intensity level 606 can be linear or non-linear, and the slope can vary. This anodal stimulation is immediately followed by a second stimulation phase comprising cathodal stimulation 608 of conventional intensity and duration. In alternative embodiments, anodal stimulation 602: (1) rises to a maximum subthreshold amplitude less than three volts; (2) is of a duration of approximately two to eight milliseconds; and/or (3) is administered over 200 milliseconds post heart beat. In yet other alternative embodiments, cathodal stimulation 608 is: (1) of a short duration; (2) approximately 0.3 to 1.5 milliseconds; (3) of a high amplitude; (4) in the approximate range of three to twenty volts; and/or (5) of a duration less than 0.3 milliseconds and at a voltage greater than twenty volts. In the manner disclosed by these embodiments, as well as those alterations and modifications which can become obvious upon the reading of this specification, a maximum membrane potential without activation is achieved in the first phase of stimulation.

Figure 7:
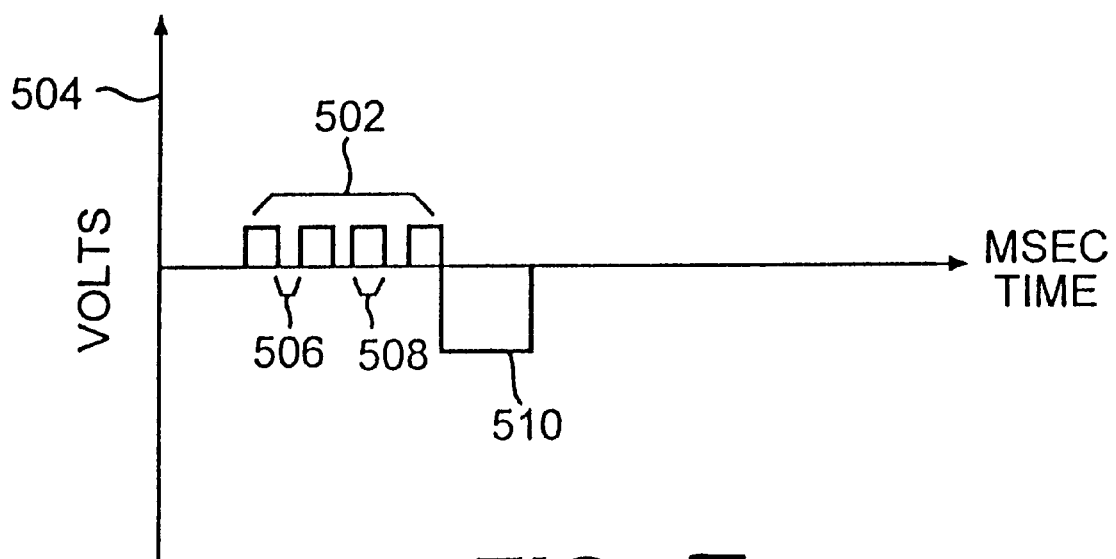
FIG. 7 is a schematic representation of leading anodal stimulation of low level and short duration, administered in series followed by conventional cathodal stimulation.

FIG. 7 depicts biphasic electrical stimulation wherein a first stimulation phase, comprising series 702 of anodal pulses, is administered at amplitude 704. In one embodiment, rest period 706 is of equal duration to stimulation period 708, and is administered at baseline amplitude. In an alternative embodiment, rest period 706 is of a differing duration than stimulation period 708, and is administered at baseline amplitude. Rest period 706 occurs after each stimulation period 708, with the exception that a second stimulation phase, comprising cathodal stimulation 710 of conventional intensity and duration, immediately follows the completion of series 702. In alternative embodiments: (1) the total charge transferred through series 702 of anodal stimulation is at the maximum subthreshold level; and/or (2) the first stimulation pulse of series 702 is administered over 200 milliseconds post heart beat. In yet other alternative embodiments, cathodal stimulation 710 is: (1) of a short duration; (2) approximately 0.3 to 1.5 milliseconds; (3) of a high amplitude; (4) in the approximate range of three to twenty volts, and/or (5) of a duration less than 0.3 milliseconds and at a voltage greater than twenty volts.

Figure 8:
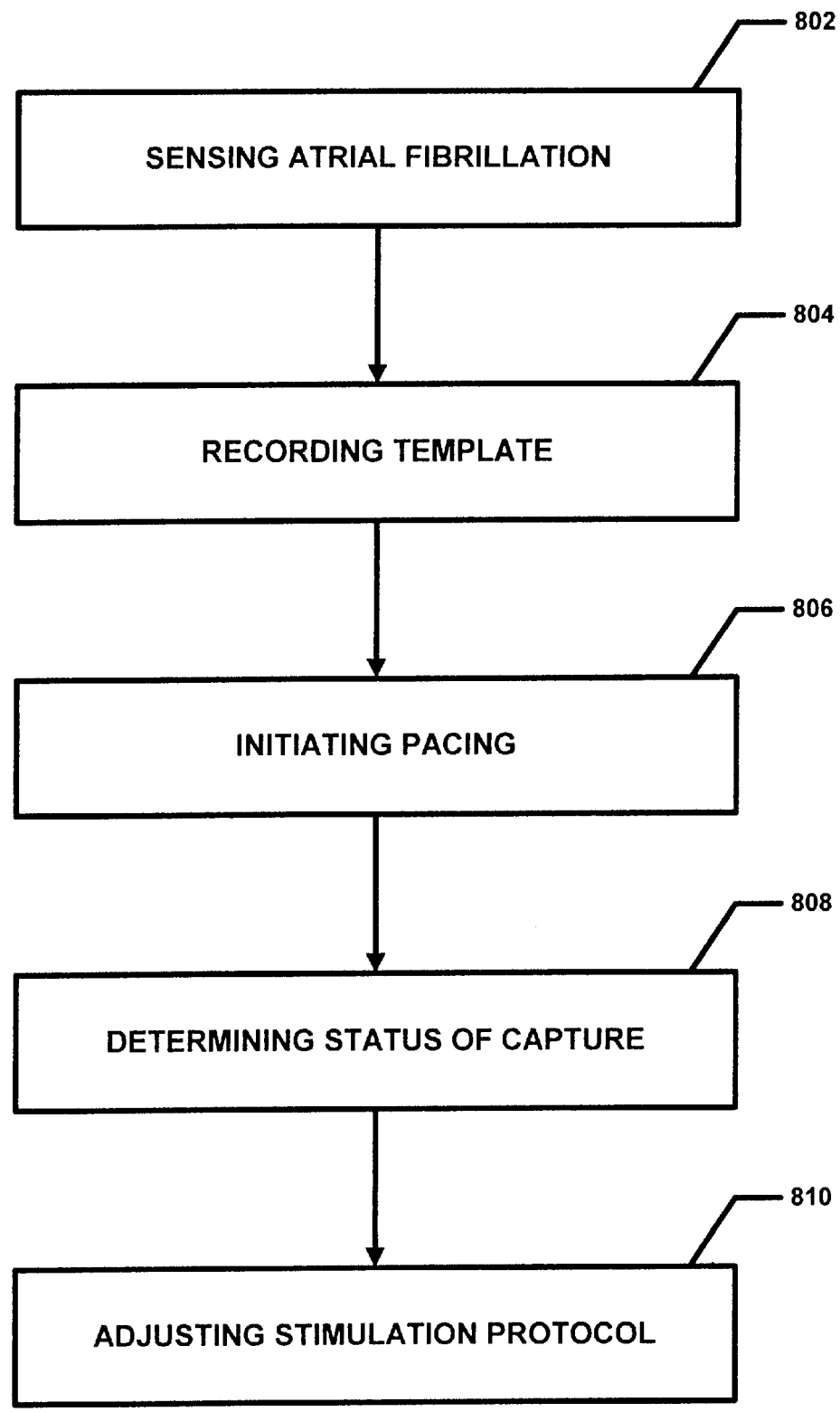
FIG. 8 illustrates the practice of the present invention.

FIG. 8 illustrates the practice of the present invention. Sensing is used to determine the existence of atrial fibrillation 802. Sensing can be direct or indirect. For example, direct sensing can be based on data from multiple atrial sensing electrodes. The sensing electrodes sense the cardiac activity as depicted by electrical signals. For example, as is known in the art, R-waves occur upon the depolarization of ventricular tissue and P-waves occur upon the depolarization of atrial tissue. By monitoring these electrical signals the control/timing circuit of the ICD can determine the rate and regularity of the patient's heart beat, and thereby determine whether the heart is undergoing arrhythmia. This determination can be made by determining the rate of the sensed R-waves and/or P-waves and comparing this determined rate against various reference rates.

Direct sensing can be based upon varying criteria; such as, but not limited to, primary rate, sudden onset, and stability. The sole criteria of a primary rate sensor is the heart rate. When applying the primary rate criteria, if the heart rate should exceed a predefined level, then treatment is begun. Sensing electronics set to sudden onset criteria ignore those changes which occur slowly, and initiate treatment when there is a sudden change such as immediate paroxysmal arrhythmia. This type of criteria would thus discriminate against sinus tachycardia. Stability of rate can also be an important criteria. For example, treatment with a ventricular device would not be warranted for a fast rate that varies, here treatment with an atrial device would be indicated.

In alternative embodiments, sensing can be indirect. Indirect sensing can be based on any of various functional parameters such as arterial blood pressure, rate of the electrocardiogram deflections or the probability density function (pdf) of the electrocardiogram. While it has been known in the art to apply pdf to the global electrocardiogram and/or to the R wave, it has been unexpectedly discovered that pdf of the baseline is also indicated for the determination of atrial abnormalities. Here, the electrodes are specific to the atrium and data related to the R wave is canceled out. Thus, whether or not to administer treatment can also be affected by pdf monitoring of the time the signal spends around the baseline.

Lastly, to determine whether an arrhythmia comes from the atria or the ventricles, a test impulse(s) can be given to one chamber to see if capture occurs and perturbs the rhythm. For example, in a ventricular rhythm, an atrial test impulse can capture the atrium, but the ventricular rhythm will continue unchanged afterwards. In an atrial rhythm, (or Sinus rhythm), if the atrial test pulse captures, the timing of all subsequent beats is changed. To determine if a pulse captures, the baseline immediately after the beat can be examined to determine if it is different from zero (or from a baseline template). If so, the beat can be inferred to have captured. In addition, the pdf pattern of the rhythm can be shown to have changed, inferring capture.

Thus, in a preferred embodiment, sensing electronics are based upon multiple criteria. In addition, the present invention envisions devices working in more than one chamber such that appropriate treatment can be administered to either the atrium or the ventricle in response to sensing electronics based upon a variety of criteria, including those described above as well as other criteria known to those skilled in the art.

If atrial fibrillation occurs, a baseline of cardiac activity or a template can be recorded 804. The template can be based on parameters such as electrocardiogram data, mechanical motion and/or probability density function data. In an alternative embodiment, the template is established after capture has occurred.

Pacing is initiated 806. In a preferred embodiment, stimulation is administered at threshold until capture has occurred, at which time stimulation is administered at a subthreshold level. In alternative embodiments, stimulation is: (1) initiated at threshold and remains at threshold; (2) initiated subthreshold and remains subthreshold; (3) conventional prior to capture and then biphasic; (4) biphasic prior to capture and then conventional or (5) biphasic throughout.

The atrium is monitored throughout this initial pacing period to determine the status of capture 808. Capture can be determined by multiple means. First, capture or the loss thereof, can be determined by monitoring cardiac rhythm. Loss of capture can result in a change in timing of the heart beat.

Second, capture or the loss thereof, can be determined through monitoring the previously described template. Where the template is established pre-stimulation, a change in the baseline signifies capture. Where the template is established after capture has occurred, a change in the template characteristics signifies loss of capture. The templates can be established and/or updated at any time.

Once capture occurs the stimulation protocol of the entrained sites is adjusted 810. In a first embodiment, the stimulation rates of the entrained sites are slowed simultaneously, and then stopped. In a second embodiment, the spread of conduction is slowed. In a third embodiment, the stimulation speed is increased and stimulation is then stopped. In addition to adjusting stimulation rates upon the occurrence of capture, the stimulation protocol can also be adjusted such that (1) if stimulation of a conventional nature was administered prior to capture, biphasic stimulation is administered post-capture; (2) if biphasic stimulation was administered prior to capture, conventional stimulation is administered post-capture or (3) if biphasic stimulation was administered prior to capture, biphasic stimulation continues to be administered post-capture.

Having thus described the basic concept of the invention, it will be readily apparent to those skilled in the art that the foregoing detailed disclosure is intended to be presented by way of example only, and is not limiting. Various alterations, improvements and modifications will occur and are intended to those skilled in the art, but are not expressly stated herein. These modifications, alterations and improvements are intended to be suggested hereby, and within the scope of the invention. Further, the pacing pulses described in this specification are well within the capabilities of existing pacemaker electronics with appropriate programming. Accordingly, the invention is limited only by the following claims and equivalents thereto.

What is claimed is:

1. A method of atrial defibrillation comprising:

sensing atrial fibrillation;

recording a baseline of cardiac activity;

stimulating the atrium using a pre-capture stimulation protocol;

determining status of capture; and stimulating the atrium using a post-capture stimulation protocol, wherein the pre-capture stimulation protocol and the post-capture stimulation protocol comprise a procedure and wherein the procedure is selected from the group consisting of pre-capture stimulation at threshold with post-capture stimulation at threshold, pre-capture stimulation subthreshold with post-capture stimulation subthreshold and pre-capture stimulation at threshold with post-capture stimulation subthreshold.

2. The method of atrial defibrillation of claim 1, wherein the procedure is further selected from the group consisting of conventional stimulation pre-capture with biphasic stimulation post-capture, biphasic stimulation pre-capture with conventional stimulation post-capture, and biphasic stimulation pre-capture with biphasic stimulation post-capture.

3. The method of atrial defibrillation of claim 2, comprising:

inserting at least two electrodes intravenously into a patient; and placing the at least two electrodes in conjunction with cardiac tissue.

4. The method of atrial defibrillation of claim 3 comprising:

locating at least one electrode in the right atrial appendage;

locating at least one electrode in the right atrial septum; and locating at least one electrode in the coronary sinus.

5. The method of atrial defibrillation of claim 4 comprising:

locating at least one electrode in the left free wall.

6. The method of atrial defibrillation of claim 3 wherein each of the at least two electrodes has an independent generator.

7. The method of atrial defibrillation of claim 3 comprising:

entraining the cardiac tissue in conjunction with each of the at least one electrodes separately; and bringing the cardiac tissue in conjunction with each of the at least one electrodes to the same phase.

8. The method of atrial defibrillation of claim 3 comprising:

sequencing the stimulation of the at least two electrodes to mimic a normal heart beat.

9. The method of atrial defibrillation of claim 3, wherein each of the at least two electrodes comprise sensing circuits and wherein the sensing circuits provide sensing data comprising:

determining the site of at least one atrial ectopic foci.

10. The method of atrial defibrillation of claim 9 wherein determining the site of at least one atrial ectopic foci comprises:
triangulating the sensing data.

11. The method of atrial defibrillation of claim 2 wherein determining status of capture comprises:
establishing a baseline of cardiac activity; and
monitoring the baseline for changes.

12. The method of atrial defibrillation of claim 2 wherein the baseline of cardiac activity comprises a template of parameters selected from the group consisting of electrocardiogram data, mechanical motion, and probability density function data.

13. The method of atrial defibrillation of claim 2 wherein biphasic stimulation comprises:
defining a first stimulation phase with a first phase polarity, a first phase amplitude, a first phase shape and a first phase duration;
defining a second stimulation phase with a polarity opposite to the first phase polarity, a second phase amplitude, a second phase shape and a second phase duration; and
applying the first stimulation phase and the second stimulation phase in sequence to cardiac tissue.

14. The method of atrial defibrillation of claim 13 wherein the first phase polarity is positive.

15. The method for electrical cardiac pacing of claim 13 wherein the first phase amplitude is less than the second phase amplitude.

16. The method for electrical cardiac pacing of claim 13 wherein the first phase amplitude is ramped from a baseline value to a second value.

17. The method for electrical cardiac pacing of claim 16 wherein the second value is equal to the second phase amplitude.

18. The method for electrical cardiac pacing of claim 16 wherein the second value is at a maximum subthreshold amplitude.

19. The method for electrical cardiac pacing of claim 18 wherein the maximum subthreshold amplitude is about 0.5 to 3.5 volts.

20. The method for electrical cardiac pacing of claim 16 wherein the first phase duration is at least as long as the second phase duration.

21. The method for electrical cardiac pacing of claim 16 wherein the first phase duration is about one to nine milliseconds.

22. The method for electrical cardiac pacing of claim 16 wherein the second phase duration is about 0.2 to 0.9 milliseconds.

23. The method for electrical cardiac pacing of claim 16 wherein the second phase amplitude is about two volts to twenty volts.

24. The method for electrical cardiac pacing of claim 16 wherein the second phase duration is less than 0.3 milliseconds and the second phase amplitude is greater than 20 volts.

25. The method for electrical cardiac pacing of claim 13 wherein the first stimulation phase further comprises a series of stimulating pulses of a predetermined amplitude, polarity and duration.

26. The method for electrical cardiac pacing of claim 25 wherein the first stimulation phase further comprises a series of rest periods.

27. The method for electrical cardiac pacing of claim 26 wherein applying the first stimulation phase further comprises applying a rest period of a baseline amplitude after at least one stimulating pulse.

28. The method for electrical cardiac pacing of claim 27 wherein the rest period is of equal duration to the stimulating pulse.

29. The method for electrical cardiac pacing of claim 13 wherein the first phase amplitude is at a maximum subthreshold amplitude.

30. The method for electrical cardiac pacing of claim 29 wherein the maximum subthreshold amplitude is about 0.5 to 3.5 volts.

31. The method for electrical cardiac pacing of claim 13 wherein the first phase duration is at least as long as the second phase duration.

32. The method for electrical cardiac pacing of claim 13 wherein the first phase duration is about one to nine milliseconds.

33. The method for electrical cardiac pacing of claim 13 wherein the second phase duration is about 0.2 to 0.9 milliseconds.

34. The method for electrical cardiac pacing of claim 13 wherein the second phase amplitude is about two volts to twenty volts.

35. The method for electrical cardiac pacing of claim 13 wherein the second phase duration is less than 0.3 milliseconds and the second phase amplitude is greater than 20 volts.

36. The method for electrical cardiac pacing of claim 13 wherein the first stimulation phase is initiated greater than 200 milliseconds after heart beat.

37. The method of atrial defibrillation of claim 2 wherein sensing atrial fibrillation comprises:
monitoring parameters selected from the group consisting of arterial blood pressure, rate of electrocardiogram deflections, and probability density function of the electrocardiogram.

* * * * *